US006444872B1

(12) United States Patent
Andersson et al.

(10) Patent No.: US 6,444,872 B1
(45) Date of Patent: Sep. 3, 2002

(54) LARGE ANIMAL MODEL OF INVASIVE PULMONARY ASPERGILLOSIS IN AN IMMUNOCOMPROMISED HOST

(75) Inventors: Borje S. Andersson; Taraneh K. Sadeghi, both of Houston; Douglas M. Cromeens, Spring; Jeffrey J. Tarrand, Houston, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/642,397

(22) Filed: Aug. 18, 2000

Related U.S. Application Data
(60) Provisional application No. 60/149,948, filed on Aug. 19, 1999.

(51) Int. Cl.$^7$ ............ A01K 67/00; A01K 67/27; G01N 33/00; G01N 33/53; A61F 2/00; C12Q 1/00
(52) U.S. Cl. ............ 800/11; 800/14; 424/423; 435/4; 435/7.2; 435/7.31
(58) Field of Search ............ 800/8, 9, 11, 14; 424/423; 435/4, 7.31, 7.2

(56) References Cited

PUBLICATIONS

K Shibuya et al., Contrib Microbio., "Animal Models of A. fumigatus Infections," 1999, vol. 2, pp. 130–138.*
Anaissie, "Opportunistic mycoses in the immunocompromised host: experience at a cancer center and review," *Clin. Infect. Dis.*, 14:S43–53, 1992.
Anaissie et al., "Emerging fungal pathogens," *Eur. J. Clin. Microbiol. Dis.*, 8:323–330, 1989.
Blazar et al., "Invasive fusarium infections in bone marrow transplant recipietns," *Am. J. Med.*, 77:645–651, 1984.
Dixon et al., "Fungus dose–dependent primary pulmonary Aspergillosis in immunosuppressed mice," *Infect. and Immun.*, 1452–56, 1989.
Eisenstein et al., "Experimental murine invasive Aspergillosis," *Am. J. Clin. Pathol.*, 93:510–15, 1990.
Epstein et al., "Studies on the pathogenesis of experimental pulmonary Aspergillosis," *Amer. J. Pathology*, 51:769–788, 1967.
Francis et al., "Efficacy of unilamellar liposomal Amphotericin B in treatment of pulmonary Aspergillosis in persistently granulocytopenic rabbits: the potential role of bronchoalveolar D–mannitol and serum galactomannan as markers of infection," *J. Inf. Dis.*, 169:356–68, 1994.

(List continued on next page.)

*Primary Examiner*—James Ketter
*Assistant Examiner*—Q Janice Li
(74) *Attorney, Agent, or Firm*—Fulbright & Jaworski LLP

(57) ABSTRACT

A model of systemic mold/Aspergillus infection in a profoundly immunocompromised host has been established in the beagle dog. The beagle was rendered immunosuppressed using a combination of total body irradiation and daily steroids, which provided a window of time where the mold could be successfully inoculated through a bronchoscope. This created a localized infection in one lung lobe, which subsequently spread diffusely throughout the lung parenchyma, and uniformly resulted in the animal's death. The invention contemplates the further study of the pathophysiology of opportunistic mold infections in vivo and also provides examples for the development of new antifungal agents and more effective combinations of agents. Finally, the invention contemplates the development of technology for the early detection of systemic mold infections. The inventors envision, that the use of the model should help save patients from clinical trials of antifungal drugs that may be effective in vitro without living up to the expectations in a clinical setting.

23 Claims, 4 Drawing Sheets

OTHER PUBLICATIONS

Hector et al., "Use of DBA/2N mice in models of systemic Candidiasis and pulmonary and systemic Aspergillosis," *Infect. and Immun.*, 1476–78, 1990.

Kurup and Sheth, "Experimental Aspergillosis in rabbits," *Comp. Immun. Microbiol. Infect. Dis.* 4:161–174, 1981.

Morrison et al., "The spectrum of non–Candida fungal infections following bone marrow transplantation," *Medicine*, 72:79–89, 1993.

Morrison et al., "Non–Candida fungal infections after bone marrow transplantation: risk factors and outcome," *Am. J. Med.*, 96:497–503, 1994.

Nawada et al., "Murine model of invasive pulmonary Aspergillosis following an earlier stage, noninvasive *Aspergillus* infection," *J. Clin. Microbiol*, 1433–39, 1996.

Pfaller and Wenzel, "Impact of the changing epidemiology of fungal infections in the 1990s," *Europ. J.Clin. Microbiol. Infect. Dis.*, 11:287–291, 1992.

Sande and Mandell, "Antimicrobial agents, antifungal and antiviral agents. I. Antifungal agents: Amphotericin B," *In: The pharmacological basis of therapeutics*, MacMillan Publishing Company Inc., New York NY, 7:1219–1239, 1985.

Spreadbury et al., "Invasive Aspergillosis: Clinical and pathological features of a new animal model," *J. Med. and Vet. Mycology*, 27:5–15, 1989.

Turner et al., "The pathogenesis of experimental pulmonary Aspergillosis in normal and cortisone–treated rats," *J. Pathol.*, 118: 65–73, 1976.

Uzun and Anaissie, "Antifungal prophylaxis in patients with hematologic malignancies. A reappraisal," *Blood*, 86:2063–72, 1995.

\* cited by examiner

LARGE ANIMAL MODEL OF INVASIVE PULMONARY ASPERGILLOSIS IN AN IMMUNOCOMPROMISED HOST

The present application claims the priority of co-pending U.S. Provisional Patent Application Ser. No. 60/149,948, filed Aug. 19, 1999, the entire disclosure of which is incorporated herein by reference without disclaimer.

BACKGROUND OF THE INVENTION

1. Field of the Invention

The present invention relates generally to the fields of pathobiology, mycology and immunology. More particularly, it concerns the design of an model animal system that is analogus to the development of human invasive pulmonary aspergillosis and, therefore, provides a useful in vivo tool for studying the pathogenesis of disseminating mold infection, as well for the development of novel antifungal agents. It also provides a tool to prospectively follow the effects of various novel therapeutic interventions against such infections.

2. Description of Related Art

Disseminated fungal infections constitute one of the most difficult challenges for clinicians caring for patients with hematological cancer (Anaissie et al., 1989). While the incidence of *Hematogenous candida* infections has been significantly reduced through the prophylactic use of azoles, such as fluconazole, infections with opportunistic molds are now a leading cause of infectious mortality in this patient population (Anaissie 1992). Aspergillosis clearly remains the most common mold infection in patients with hematological cancer, with *Aspergillus fumigatus* being the offending cause in more than 90% of the infected patients. However, new opportunistic pathogens also have emerged worldwide as causing life-threatening infection, the most frequently reported of which is Fusarium spp. (Morrison et al., 1993; Morrison et al., 1994; Pfaller et al., 1992; Blazar et al., 1984; Uzun et al., 1995). Infections with Fusarium are associated with a very high mortality risk, and this mold is typically refractory to Amphotericin B, the standard therapy for disseminated mold infections. Since infection with this organism may mimic aspergillosis, patients are usually treated with Amphotericin B (AMB), an agent with poor activity against fusariosis. Further, similar to the case of Aspergillus infection, the airways are the most common primary site of inoculation/infection and are almost always involved in disseminated disease (Morrison et al., 1993; Morrison et al., 1994; Pfaller et al., 1992; Blazar et al., 1984; Uzun et al., 1995).

It has recently been suggested that the addition of gamma-interferon and/or GM-CSF might enhance the efficacy of AMB against opportunistic mold infections. This is important, since AMB by itself has only borderline efficacy against molds. Further, AMB treatment for documented or suspected systemic mold infections carries with it common (in >75% of the cases), substantial and frequently dose-limiting nephrotoxicity, occasionally serious enough to warrant hemodialysis. The acute infusion-related adverse events (severe shaking chills, fever, nausea, vomiting, and headache) also are quite troublesome to patients. Less common side effects encountered with the use of AMB include cardiac arrhythmia, bone marrow suppression, neuropathies, and convulsions (Sande et al. 1985).

Mold infections continue to pose a serious threat to the recovery of immunosuppressed patients who have undergone chemotherapy or radiotherapy. Thus, in addition to finding new and more effective antifungal antibiotics, the need for an animal model of systemic aspergillosis has been deemed valuable by many investigators in the art to improve an understanding of the pathophysiology of mold infections. The literature contains a multitude of reports describing invasive aspergillosis in small animal's, such as mice, rats, and rabbits (Epstein et al., 1967; Dixon et al., 1989; Hector et al., 1990; Eisensten et al., 1990; Nawada et al., 1996; Turner et al., 1976; Kurup et al., 1981; Spreadbury et al., 1989; Francis et al., 1994). These reports clearly demonstrate the principle that an Aspergillus infection can be established in an experimental animal. However, none of these described models can be claimed to be clinically relevant, since the animal's typically have been exposed to extraordinarily high fungal loads, and in most instances have been immunosuppressed with steroids alone (Epstein et al.; 1967, Hector et al., 1990; Nawada et al.; 1996, Kurup et al., 1981). Further, in all described models known to the inventors of the present invention, the fungal load is either infused intravenously or spread through intranasal injection to the lungs through the trachea or directly injected into the trachea transcutaneously. This produces a diffuse pulmonary infection, which is very different from what is typically encountered in an immunocompromised human patient. Thus, there is no available animal model that has a close similarity to the human clinical situation.

SUMMARY OF THE INVENTION

To overcome these and other deficiencies in the art, the present inventors have developed a model which closely resembles the clinical situation where a human patient, who has undergone intensive chemotherapy or radiotherapy as treatment of a malignancy, or as preparation for hemopoietic stem cell transplantation, subsequently suffers a mold infection.

Thus, the model developed is analogous to the commonly observed human situation, where the infection starts with a localized lesion and then disseminates to involve a majority of the pulmonary tissue, leading to the animal's demise. The infective lesion often manifests as development of pneumonia in the animal model and in humans.

The development of a clinically relevant model for immunocompromised patients with systemic mold infections permits:

acquisition of an increased understanding of the pathophysiology of systemic fungal infections, such as is warranted to design new and more effective strategies for the prevention and treatment of these infections in immunocompromised human patients;

obtaining a "testing vehicle" for the preclinical screening of novel antifungal agents and also for testing the efficacy of combinations of interventions to control an already established infection. This is of importance as it avoids unnecessary and cumbersome clinical trials where patients might otherwise suffer suboptimal treatment for their infection;

development of new methods for early detection of mold infections; and obtaining a model for the long-term follow-up of the treatment of an established systemic fungal infection.

In a preferred embodiment the mold infection is by Aspergillus spp. The animal used herein as a the model animal is a beagle.

An important feature of the invention is that the animal model developed herein is reproducible. Thus, in one embodiment, longitudinal and systematic studies on the pathophysiology of the infection may be performed using the model.

In one important embodiment, the model may be used to develop or test new antifungal agents in vivo. In a specific example, the inventors present evidence for the testing of a new antifungal agent, Natamycin, using the model. In another embodiment, the model can be used to develop effective antifungal therapies, such as the use of combination drugs in vivo. In yet another embodiment, this in vivo model may be used to tailor the antifungal therapy to the anticancer therapy that the patient would be undergoing. The model developed herein also may be used for the development of long-term follow-up treatments. Primarily, the inventors envision that the use of this model should help save patients from clinical trials of antifungal drugs that may be effective in vitro without living up to the expectations in a clinical setting.

In a related embodiment, the model developed in the present invention can be used to develop methods for the early detection of Aspergillus infection.

Thus, the invention describes the use of a beagle, which is accepted by both the NCI and the FDA for safety studies of pharmaceutically active agents prior to entering clinical trials, as a clinical model for an immunocompromised patient that contracts a systemic mold infection. In alternate embodiments, the inventors also contemplate the use of other large animal's, such as dog, pig, sheep, monkey, or chimpanzee for the animal model.

In one preferred embodiment of the invention, immunosuppression in a beagle is achieved by total body irradiation (TBI). In one specific embodiment, the TBI is achieved using an X-ray (Cobalt) source. The X-ray therapy (XRT), can be followed with daily oral steroid administration to further suppress T-lymphocyte and macrophage function and enhance spreading the infection. In alternative embodiments, the use of immunosuppressant steroids prior to the TBI is also contemplated. One of the steroids that may be used effectively is prednisolone. However, one of skill in the art will recognize that the use of other immunosuppressant steroids, such as hydrocortisone, betamethazone, glucocorticoid analogs, and others is also possible. As an alternative to steroids, the use of other T-cell suppressive agents such as anti-T-lymphocyte globulin (ATG), and/or nucleoside analogs (e.g. fludarabine), and/or immunophilins (e.g. Cyclosporin A or rapamycin) also are contemplated. The infective agent used to infect the model animal is a mold species. In a specific embodiment, the mold species chosen to infect the beagles is any one of the Aspergillus spp. In a preferred embodiment of the invention the mold species chosen is *Aspergillus fumigatus*. *Aspergillus fumigatus* accounts for over 90% of the human clinical infections. In alternative embodiments, any Aspergillus spp. that cause human clinical infections may be used.

In another preferred embodiment of the invention, the beagle is infected by Aspergillus spores. In a related aspect of the invention, the infection with spores is repeated on more than one occasion. In another related embodiment, the Aspergillus spores are encapsulated in small agarose beads. Alternatively, the mold spores may be encapsulated in other formulations used for encapsulation purposes as are known to those of skill in the art. Aspergillus spores so encapsulated provide a standardized dosage and can be cryopreserved by techniques known in the art to obtain a stock of a reproducible dosage of infectious inoculum.

An important aspect of the invention relates to the administration of the infective mold in a manner as to obtain a localized infective lesion in the model animal which is similar to the initial infection developed in immunosuppressed human patients. Thus, the mold administration is performed herein using a pediatric bronchoscope to safely and reproducibly introduce the mold in the intermediary (lower) right lung lobe.

In one embodiment of the invention, the time of mold administration to the beagle is at the time of leukopenia. In another embodiment of the invention, the time of mold administration to the beagle is at the time of profound immunosuppression. In a related aspect, the time of mold administration to the beagle is 6, 7, 8, 9, 10, 11, 12, 13, 14, 15, 16, 17, 18, 19, 20, 21, 22 or 23 days after TBI or more preferable 10–14 days after TBI. In other aspects, the time of mold administration is when the animal's neutrophil count is about <400 per $\mu$L.

In other aspects, prophylactic oral antibiotics are administered to the immunosuppressed beagles to prevent the development of secondary bacterial infections. The antibiotics used can be broad-spectrum. In several cases, the antibiotic regimen is changed as deemed necessary to obtain better antibacterial coverage, while still allowing for the mold infection to progress. In related aspects of the invention, prophylactic platelet transfusions are administered to the immunosuppressed beagles used in the model system to prevent bleeding.

It is envisioned that this model system may be suitably adapted for studying a variety of mold infections, and developing novel antifungal drugs in immunocompromised patients such as patients undergoing BMT, chemotherapy, broad-spectrum antibiotics, cytotoxic therapy, immunosuppressants, patients with AIDS, or/and patients with intravascular catheters.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. A. Prior to inoculation, normal X-ray, FIG. 3. B.

Immediately after inoculation with Aspergillus spores, the arrow points to the site where the inoculum was deposited, FIG. 3. C. Five days post inoculation, the arrow points to the early progressive infiltrate/pneumonia in the lower right lung, FIG. 3. D. Nine days post inoculation, the animal has now developed a rapidly progressive pneumonia that involves virtually the entire right lung and has started to spread to the left lung. Arrows point to the center of the infection in the corner half of the right lung.

Figure 1A:
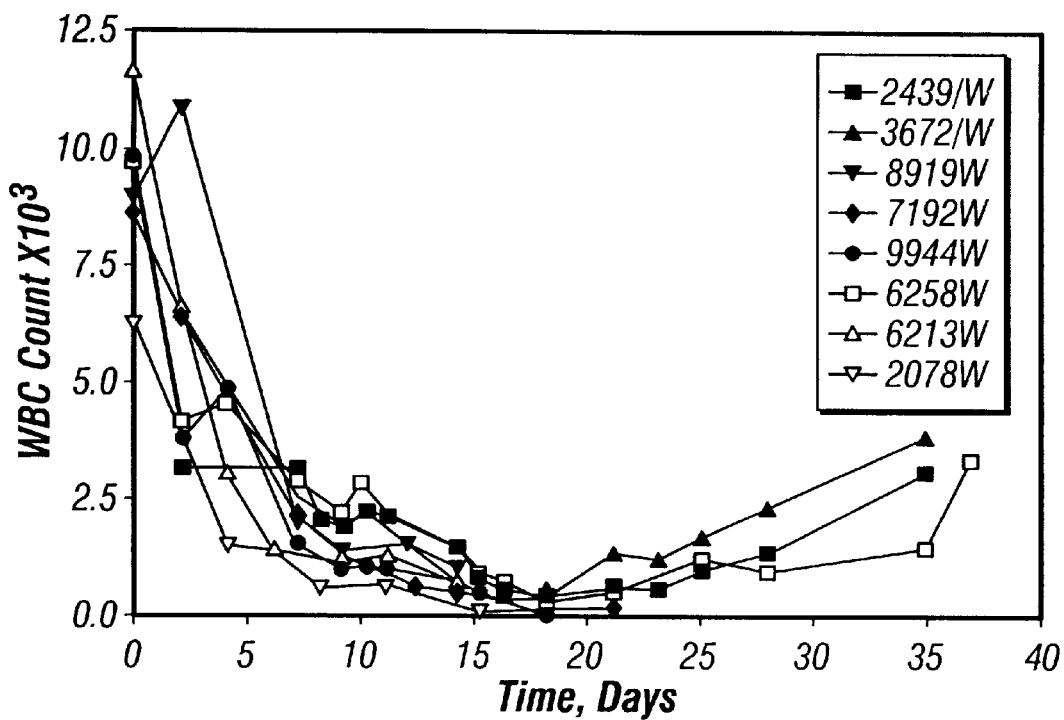
FIGS. 1A and B. Time course for the pattern of leukopenia after administration of 2.1–3.0 Gray of total body irradiation, FIG. 1.A. Total white blood cell count, and FIG. 1.B. Absolute neutrophil count. The time period during which the mold inoculum is administered is about days 10 to days 14 with day 0 being the day the XRT is administered.
Figure 1B:
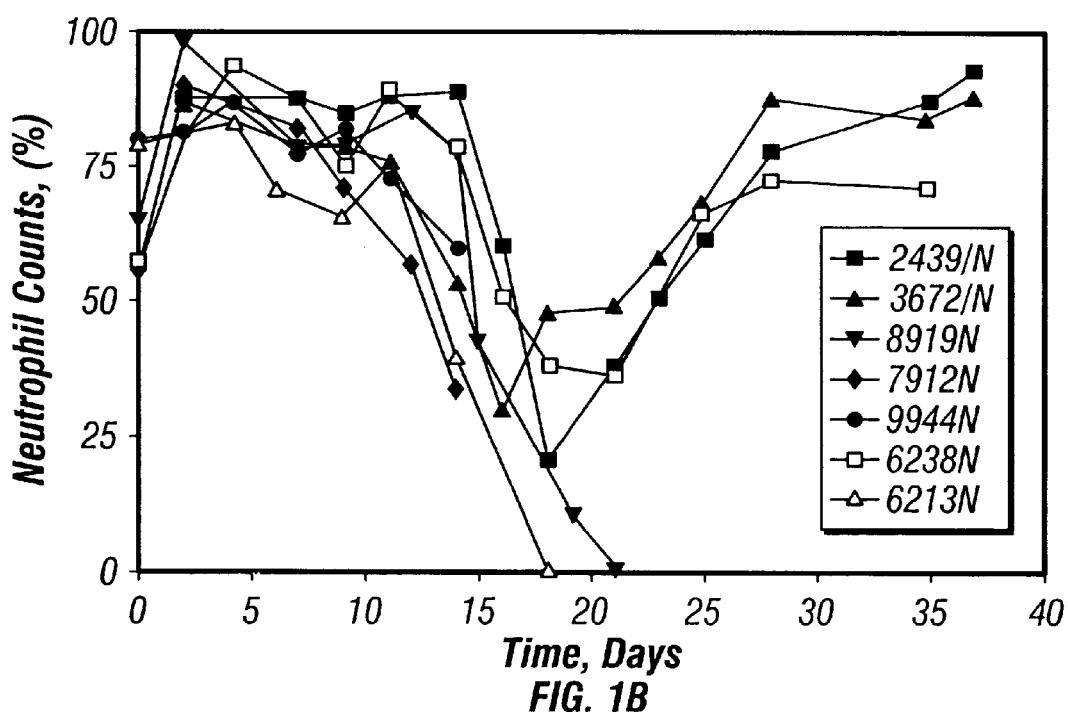
Figure 2:
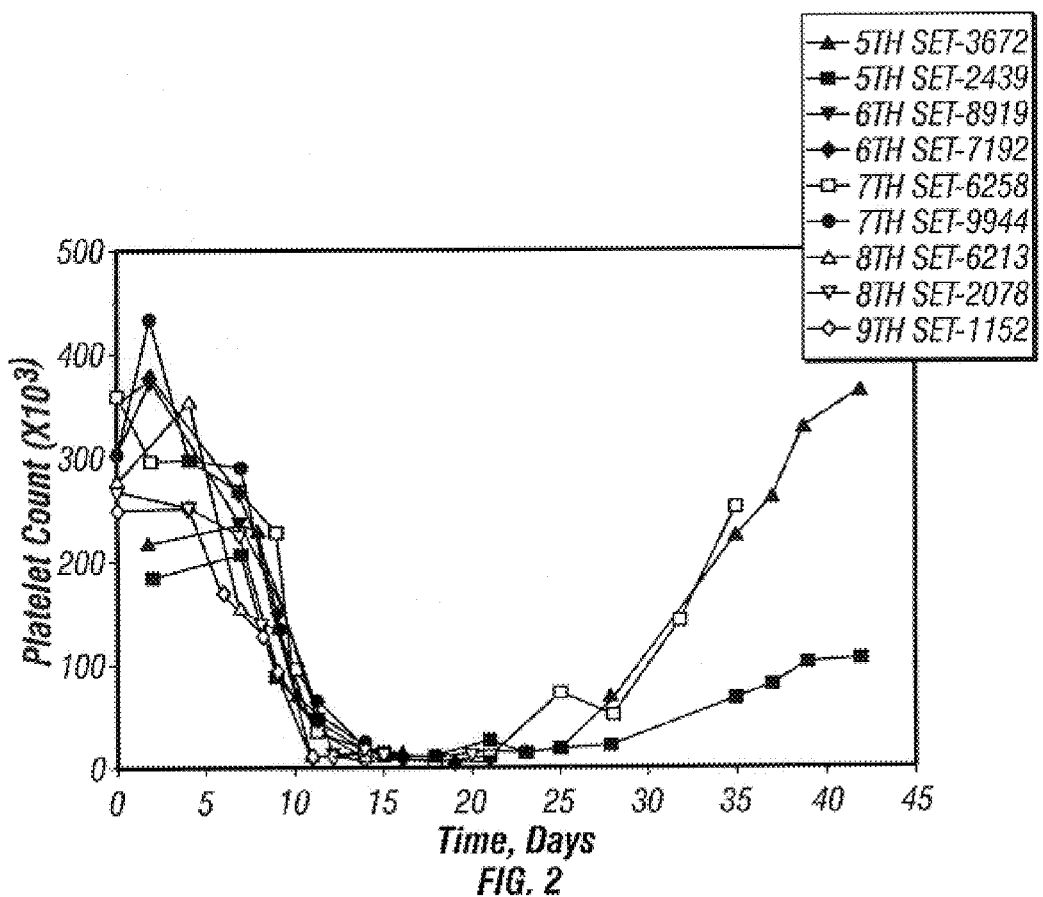
FIG. 2. Time course for the pattern of thrombocytopenia after of 2.1–3.0 Gray of total body irradiation. XRT is administered on designated day 0.
Figure 3A:
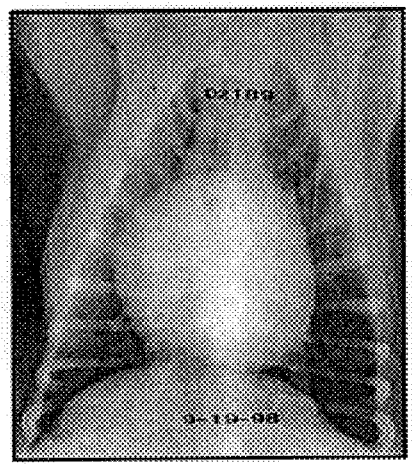
FIGS. 3 A, B, C, and D. Sequential chest radiographs of one dog that was inoculated with Aspergillus 10 days after TBI, and subsequently developed a lethal progressive mold pneumonia.
Figure 3B:
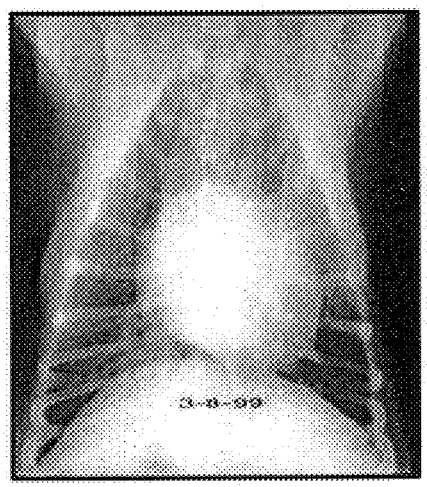
Figure 3C:
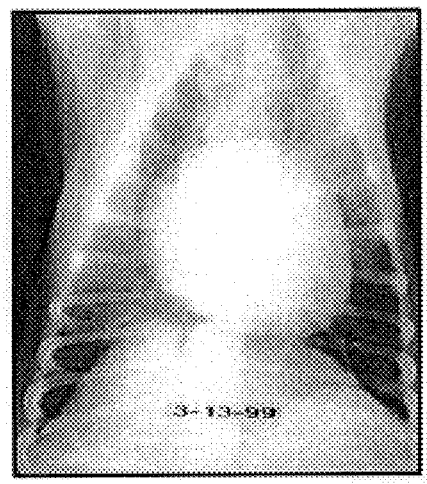
Figure 3D:
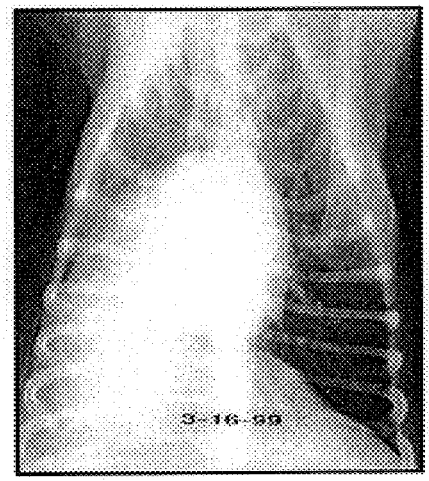
Figure 4A:
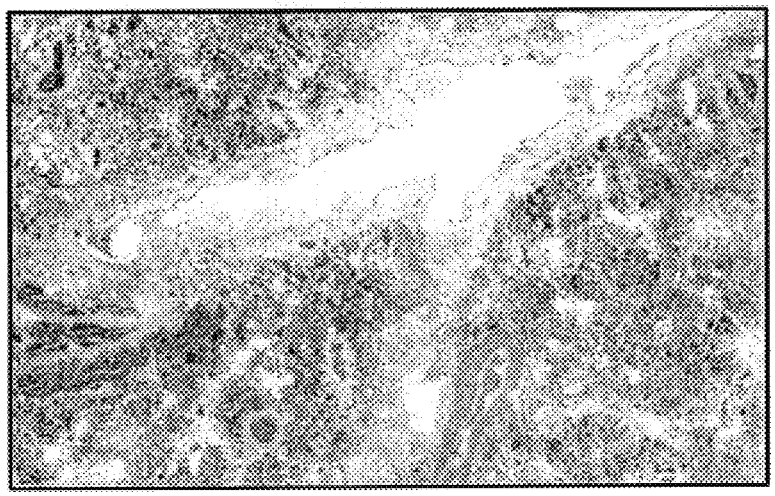
Figure 4B:
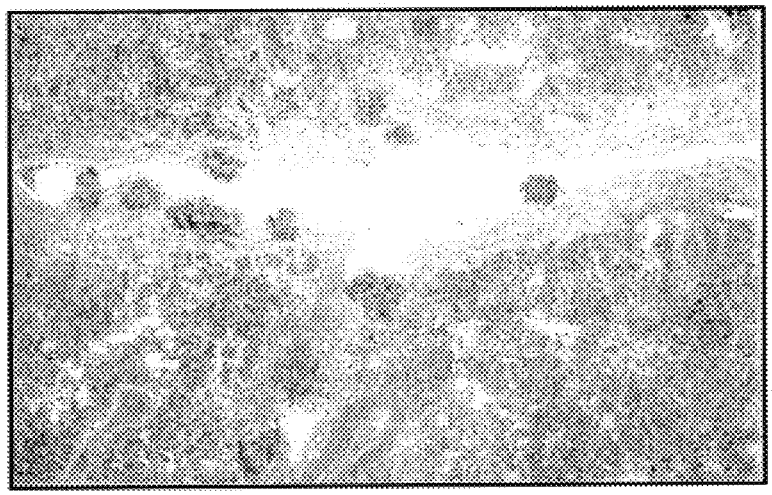
Figure 4C:
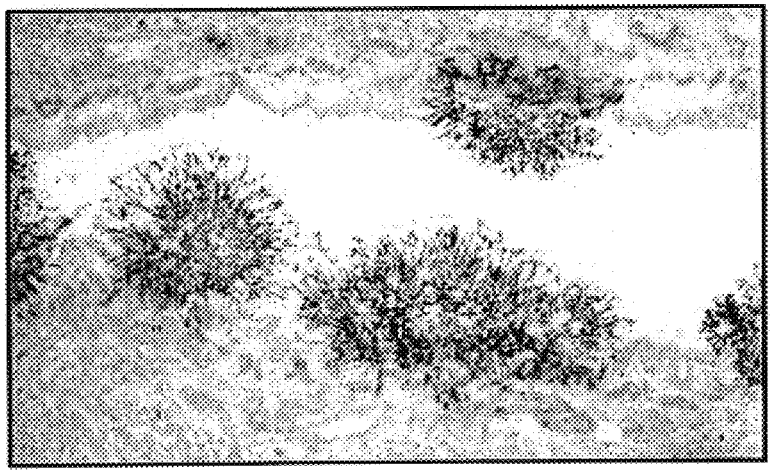

FIGS. 4 A, B and C. Lung tissue specimen obtained at necropsy from dog with established pneumonia. FIG. 4. A. Hematoxylin and eosin stain, low power magnification: hemorrhagic, necrotic regions with consolidation are abundant. In the main bronchus' air-filled space small rounded lesions can be seen, sticking to the bronchial wall. FIG. 4. B. Special (silver-based) stain of the area in FIG. 4A. showing the rounded areas to be compatible with fungal (mold) lesions (black in this special stain). FIG. 4. C.

Silver stain (high power magnification) showing the branched hyphae that are diagnostic of a mold/Aspergillus infection, same tissue section as in figures FIG. 4.A. and FIG. 4.B. The invasive growth pattern of these lesions is well visualized. Necropsy tissue was also sent for in vitro culture and subtyping of the specific mold that was observed, confirming that the observed infection in this animal was indeed *Aspergillus fumigatus*, compatible with the administered organism (not shown).

DESCRIPTION OF ILLUSTRATIVE EMBODIMENTS

A. THE PRESENT INVENTION

The present invention involves methodology for creating an immunocompromised large animal model that is susceptible to mold infection. Initially, a limited infectious lesion is established, which gradually progresses and uniformly results in the animal's death. The bone marrow and general immunosuppression is severe enough that the dogs are dependent on supportive measures including prophylactic antibiotics and platelet transfusions for approximately two weeks before their bone marrow and immune system would recover. This closely resembles the situation of a human patient undergoing cancer therapy. Therefore, the present invention consists of a large animal model of an immunocompromised host that closely adheres to the human clinical situation where patients undergoing chemotherapy and/or X-ray therapy (XRT) often become sufficiently immunocompromised to acquire an opportunistic mold infection. The inventors envision that this model will allow the longitudinal and systematic investigation of the pathophysiology of mold infections. Furthermore, the inventors contemplate the use of this in vivo model system in investigating therapies for opportunistic mold infections in immunocompromised humans, wherein the immunosuppression may be developed under various conditions, such as but not limited to, humans undergoing cancer therapy; humans undergoing immunosuppressive therapy prior to a bone-marrow transplant (BMT); humans undergoing immunosuppressive therapy prior to organ transplantations; and/or humans infected by the HIV virus. The inventors contemplate the use of this model system to develop new antifingal therapies, such as novel antifungal agents and novel combination antifungal therapies, with a high propensity for clinical efficacy. The model allows these therapies to be effectively designed in concert with ongoing cancer therapies which are known to those of skill in the art. The inventors also contemplate the use of this animal model system to develop new methods for early detection of Aspergillus infections and for the long-term prognosis and follow-up of treatment results.

Due to its close similarity with the human situation the inventors contemplate that this model can be used to achieve the following:

1. To acquire an increased understanding of the pathophysiology of systemic fungal infections, such as is warranted for the design of new and more effective strategies for treating opportunistic mold infections in immunocompromised humans.
2. As a "testing vehicle" for the preclinical screening of novel antifungal drugs and for testing the efficacy of combinations of drugs to control an established infection. This will save patients clinical trials of new but suboptimal antifungal therapy.
3. As a medium to develop technology for early detection of mold infections and also for longitudinal follow-up of the treatment of an already established mold infection.

The use of a large animal such as a beagle dog with the goal of creating a model that closely resembles the human situation after chemotherapy or radiotherapy has not been previously explored, although less well defined models have been described in mice, rats, and rabbits (Epstein et al., 1967, Hector et al., 1990, Nawada et al., 1996, Kurup et al., 1981, Spreadbury et al., 1989, Francis et al., 1994). The inventors present herein several studies which include immunosuppressing the beagles with a series of different doses of X-ray therapy (XRT) administered as total body irradiation (TBI) and/or steroids, which demonstrate that in this very complex model it is possible to control all necessary parameters (see seven parameters as listed in Example 1), such that the inventors can reproducibly induce an initially localized, but subsequently progressive infective lesion which leads to the animal's death. The infective lesion is sometimes (but not always) manifest as pneumonia. The results of the experiments are illustrated in FIGS. 1, 2, 3 and 4 and in Table 1. Animal's that received 2.1 Gy of TBI+ steroids lived beyond day 30 without developing pneumonia and recovered bone marrow function. Of the two dogs that were treated at 2.5 Gy+steroids one animal did not develop radiographic signs of pneumonia, and one dog developed a localized pneumonia which regressed and healed when the dog recovered his immune function. At a TBI dose of 3.0 Gy+prednisolone, all dogs developed pneumonia and died. However, three of the first four dogs treated at this TBI dose died from secondary bacterial infection. The dogs also suffered intestinal bleeding complications, which may have contributed to the development of a systemic bacterial superinfection. The addition of prophylactic antibiotics and platelet transfusions made it possible to observe the natural course of a progressive mold infection without the confounding effect of the bacterial superinfection.

None of the previously published small animal models demonstrate a consistent development of an initial localized infection that gradually and uniformly progresses to a widespread lethal infection. With the exception of the use of an overwhelming dose of the infectious agent, which led to 100% lethality in one of the described small animal models, no consistent and reproducible model for opportunistic mold infection in immunocompromised hosts exists. Thus, the inventors' model described herein, is unique and different in this aspect, since it offers a completely controlled design and allows a complete reproducibility of the attainment of the systemic fungal infection, with a close resemblance to the clinical scenario observed in humans undergoing immunosuppressive therapy.

The section of Examples is presented to illustrate the various parameters taken into account during the development of the model and to demonstrate the effects obtained when varying the different parameters that may influence the animal's outcome after immunosuppression combined with mold administration.

B. FUNGAL INFECTIONS

Immunocompromised patients are particularly susceptible to fungal infections. In those patients, fungal organisms may cause infections that are difficult to eradicate. Immunocompromised patients include, for example, those infected by HIV, those undergoing chemotherapy, transplant recipients, or cancer patients receiving immunosuppressive medications.

Fungal and other mycotic pathogens (some of which are described in Human Mycoses, E. S. Beneke, Upjohn Co.: Kalamazoo, Mich., 1979; Opportunistic Mycoses of Man and Other Animals, J. M. B. Smith, CAB International: Wallingford, UK, 1989; and Scrip's Antifungal Report, by PJB Publications Ltd, 1992) are responsible for a variety of diseases in humans, ranging from mycoses involving skin, hair, or mucous membranes, such as, but not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmaris), Tinea pedis, Tinea unguium, Torulopsosis, Trichomycosis axillaris, White piedra, and their synonyms, to severe systemic or opportunistic infections, such as, but not limited to, Actinomycosis, Aspergillosis, Candidiasis, Chromomycosis, Coccidioidomycosis, Cryptococcosis, Entomophthorarnycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, Absidia spp., *Actinomadura madurae*, Actinomyces spp., *Allescheria boydii*, Alternaria spp., *Anthopsis deltoidea, Apophysomyces elegans, Arnium leoporinum*, Aspergillus spp., *Aureobasidium pullulans, Basidiobolus ranarum*, Bipolaris spp., *Blastomyces dermatitidis*, Candida spp., Cephalosporium spp., Chaetoconidium spp., Chaetomium spp., Cladosporium spp., *Coccidioides immitis*, Conidiobolus spp., *Corynebacterium tenuis*, Cryptococcus spp., *Cunninghamella bertholletiae*, Curvularia spp., Dactylaria spp., Epidermophyton spp., *Epidermophyton floccosum*, Exserophilum spp., Exophiala spp., Fonsecaea spp., Fusarium spp., Geotrichum spp., Helminthosporium spp., Histoplasma spp., Lecythophora spp., Madurella spp., *Malassezia furfur*, Microsporum spp., Mucor spp., *Mycocentrospora acerina*, Nocardia spp., *Paracoccidioides brasiliensis*, Penicillium spp., Phaeosclera dematioides, Phaeoannellomyces spp., *Phialemonium obovatum*, Phialophora spp., Phoma spp., *Piedraia hortai, Pneumocystis carinii, Pythium insidiosum, Rhinocladiella aquaspersa, Rhizomucor pusillus*, Rhizopus spp., *Saksenaea vasiformis, Sarcinomyces phaeomuriformis, Sporothrix schenckii, Syncephalastrum racemosum, Taeniolella boppii*, Torulopsosis spp., Trichophyton spp., Trichosporon spp., *Ulocladium chartarum, Wangiella dermatitidis*, Xylohypha spp., Zygomyetes spp. and their synonyms. Other fungi that have pathogenic potential include, but are not limited to, *Thermomucor indicae-seudaticae*, Radiomyces spp., and other species of known pathogenic genera. These fungal organisms are ubiquitous in air, soil, food, decaying food, etc. Histoplasmoses, Blastomyces, and Coccidioides, for example, cause lower respiratory infections. *Trichophyton rubrum* causes difficult to eradicate nail infections. In some of the patients suffering with these diseases, the infection can become systemic causing fungal septicemia, or brain/meningal infection, leading to seizures and even death.

Fungal organisms which attack immunocompromised patients are often called "opportunistic fungi." These may be opportunistic yeast's or other molds, such as described above.

Aspergillosis is the most common mold infection in patients with hematological cancer, with *Aspergillus fumigatus* being the offending cause in more than 90% of the infected patients. Aspergillosis is a term that encompasses a variety of disease processes caused by Aspergillus species. Aspergillus species are ubiquitous; their spores are constantly being inhaled. Of the more than 300 species known, only some are ordinarily pathogenic for man and these include: *A. fumigatus, A. flavus, A. niger, A. nidulans, A. terreus, A. sydowi, A. flavatus*, and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of eases, there is hematogenous spread to other sites. Aspergillosis is also a rare but devastating complication of traumatic wounds, such as, bum wounds, frost bite wounds, or wounds developed by diabetics, where amputation is often required for cure. Invasive aspergillosis is commonly fatal, so aggressive diagnosis and treatment is required. Detection of Aspergillus infection is difficult as blood, urine and cerebrospinal fluid cultures are rarely positive, however, the fungi can be seen in smears and biopsies from infected tissue.

C. CANCER THERAPIES

A wide variety of cancer therapies, known to one of skill in the art, may be used in combination with the antifungal agents contemplated of to be tested using the model of the present invention. The inventors can use any of the treatments described herein on the beagle while evaluating the efficacy of novel antifungal agents in the immunosuppressed beagles to mimic the clinical situation where a human patient is subject to any of these cancer therapies.

Radiotherapeutic Agents

Radiotherapeutic agents and factors include radiation and waves that induce DNA damage for example, $\gamma$-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, surgery or sham surgery may be used in the model in the context of the present invention. Chemotherapeutic Agents These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

Antibiotics

Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11 -trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fingoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11 -trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Bleomycin

Bleomycin is a mixture of cytotoxic glycopeptide antibiotics isolated from a strain of Streptomyces verticillus. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

Miscellaneous Agents

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m² for 5 days every three weeks for a total of three courses. Exemplary doses may be 0.50 mg/m², 1.0 mg/m², 1.50 mg/m², 1.75 mg/m², 2.0 mg/m², 3.0 mg/m², 4.0 mg/m², 5.0 mg/m², 10 mg/m². Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

VP16

VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m² or as little as 2 mg/m², routinely 35 mg/m², daily for 4 days, to 50 mg/m², daily for 5 days have also been used. When given orally, the dose should be doubled. Hence the doses for small cell lung carcinoma may be as high as 200–250 mg/m². The intravenous dose for testicular cancer (in combination therapy) is 50 to 100 mg/m² daily for 5 days, or 100 mg/m² on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor

Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

Plant Alkaloids

Taxol

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m² per day for 5 days or 210 to 250 mg/m² given once every 3 weeks. Of course, all of these dosages are exemplary, and any dosage in-between these points is also expected to be of use in the invention.

Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m² of body-surface area, weekly, and prednisolone, orally, 40 mg/m², daily. Adult patients with Hodgkin's disease or non-Hodgkin's lymphomas usually receive vincristine as a part of a complex protocol. When used in the MOPP regimen, the recommended dose of vincristine is 1.4 mg/m². High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m² can be administered or 1.5 to 2 mg/m² can also be administered. Alternatively 0.02 mg/m², 0.05 mg/m², 0.06 mg/m², 0.07 mg/m², 0.08 mg/m², 0.1 mg/m², 0.12 mg/m², 0.14 mg/m², 0.15 mg/m², 0.2 mg/m², 0.25 mg/m² can be given as a constant intravenous infusion. Of course, all of these dosages are exemplary, and any dosage in-between these points is also expected to be of use in the invention.

Vinblastine

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can given. Of course, all of these dosages are exemplary, and any dosage in-between these points is also expected to be of use in the invention.

Alkylating Agents

Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Cannustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Cannustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject Melphalan Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject Cyclophosphamide Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil

Chlorambucil (also known as leukeran) was first synthesized by Everett e[009f] al. (1953). It is a bifinctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remingtons Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan Busulfan (also known as myleran) is a bifinctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

D. IMMUNOSUPPRESSION

Immunosuppression of animals in this invention is performed by a combination of total body irradiation and steroids. However, other methods of immunosuppression are known in the art and may be employed to immunosuppress animals.

Radiation

Total body irradiation achieves wide and complete immunosuppression. Several protocols are known in the art for administering TBI. Generally, one can place the beagle in a special box to obtain uniform radiation exposure. The X-ray (cobalt) therapy is the most preferred embodiment. Dosages were chosen to allow the beagles to be immunocompromised before infection with the mold and ranged from about 2.0–3.0 Gy. However, higher doses of TBI also may be used.

Other forms of radiations that may be used to achieve TBI include, for example, γ-irradiation, X-rays, UV-irradiation, microwaves, electronic emissions, radioisotopes, and the like. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Steroids and Other Immunosuppressants

Chemical immunosuppression in mammals can be produced by any of a variety of reagents including myelosuppressive alkylating agents such as cyclophosphamide, antimetabolites such as 5-fluoro-uracil, plant alkaloids such as vinblastin, antibiotics such as doxorubicin, triamcinolone acetonide, cyclosporins, cytochalasin and a wide variety of steroids such as hydrocortisone acetate, betamethazone, cortisone acetate. Alternatively the use of other T-cell suppressive agents such as anti-T-lymphocyte globulin (ATG), and/or nucleoside analogs (e.g. fludarabine), and/or immunophilins (e.g. Cyclosporin A or rapamycin) are also contemplated. These agents are typically administered i.p, i.m., i.v. or s.c., depending on the pharmacological properties of the agent. Administration is carried out on a regular basis, the frequency of which is sufficient to maintain the mammal in a constant state of immunosuppression over the time frame of the experiment.

Combinations

To achieve an immunosuppressed condition the beagles used can be treated with various combinations of different immunosuppressants. For example, in a preferred embodiment the inventors use total body irradiation (TBI) with X-ray (cobalt) at a dose of 2.0–3.0 Gy followed by administering steroids (described in Examples). Alternatively, one can initiate the immunosuppression by administering steroids, and follow this with TBI. In yet another alternative, one can achieve the immunosuppression by a simultaneous treatment with steroids and TBI.

The steroid or other immunosuppressant agent based treatment may precede or follow the irradiation treatment by intervals ranging from minutes to days to weeks. In embodiments where the steroid or other immunosuppressant agent and TBI are administered together, one would generally ensure that a significant period of time did not expire between the time of each delivery. In such instances, it is contemplated that one would administer to the beagle both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either steroid or other immunosuppressant agent or the TBI will be required to achieve the level of immunosuppression desired. Various combinations may be employed, where steroid or other immunosuppressant agent treatment is "A" and the TBI is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations also are contemplated.

In addition, the immunosuppressive regimen can be administered to a animal in conjunction with other therapeutic methods such as standard cancer/tumor therapies or AIDS treatments to obtain the equivalent of a human clinical situation. For example, the immunosuppressive regimen can be administered in conjunction with a sham surgical procedure mimicking excision of a tumor, and/or with radiation therapy, chemotherapy, immunotherapy, genetherapy and/or local heat therapy. The exact dosages and regimens can be suitable altered by those of ordinary skill in the art.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Parameters for the Development of The Model

The inventors describe the development of a model which shows consistent and reproducible development of mold infection in an immunosuppressed beagle as is observed in human clinical counterparts. A variety of parameters that were completely controlled leading to the consistency of the model are described below:

1. The "Right" Animal: While choosing an animal the inventors had to consider that a human/clinical mold infection, such as an Aspergillus infection, usually begins as a localized infection and not as a widespread and diffuse pulmonary infection. To be able to reproducibly inoculate a specified dose of an infectious agent in a limited, defined part of the airways the inventors must have easy access to a particular part of the pulmonary tree. This meant that a large animal, such as dog, pig, sheep or monkey, rather than a rodent or lagomorph should be considered. The beagle, which is accepted by both the NCI and the FDA for safety studies of pharmaceutically active agents prior to entering clinical trials, was favored. This dog is easily accessible from several commercial breeders, and in addition to the selected experimental dogs one could conveniently house extra animal's for donation of both platelets and red cells to be transfused as needed during the supportive care phase of the experiments, i.e. after the mold administration.

2. Immunosuppression: For immunosuppression the inventors chose total body irradiation (TBI) with an X-ray (Cobalt) (XRT) source, administered with the animal under general anesthesia in a specially constructed box to obtain uniform radiation exposure. The XRT can be standardized to within at most 5% of an intended dose, which is superior to any cytotoxic drug treatment that might be considered for immunosuppressive purpose. Further, the XRT dose can be calculated such that it gives a window of fairly deep immunosuppression sustained for 3–5 weeks, which should be sufficient for the intended purpose. The XRT was followed with daily oral prednisolone administration to further suppress T-lymphocyte and macrophage function and enhance spreading the infection.

3. Mold Species: More than 90% of human clinical Aspergillus infections are a result of *Aspergillus fumigatus* infection. Hence, this species of mold was chosen.

4. Mold Dose: To standardize the mold dosage, the inventors prepared batches of Aspergillus spores that were mixed in agarose and stirred down vigorously in mineral oil to obtain a suspension of spores encapsulated in small agarose beads (the approximate average bead diameter was 20 $\mu$m). After washing the beads in 0.5% deoxycholate, they were mixed with glycerol prior to cryopreservation and storage at −70° C. The use of agar beads and other encapsulation methods are also contemplated.

5. Mold Administration: The human clinical infection usually starts as a localized airway infection either in the sinuses or in a part of one lung, and not as a generalized pulmonary infection. The inventors decided to utilize a pediatric bronchoscope to safely and reproducibly introduce the Aspergillus spores in the intermediary (lower) right lung lobe. After standardization of the dose, $1 \times 10^6$ spores encapsulated in agarose beads and resuspended in NS were infused at each occasion.

6. Time of Mold Administration: In most human patients, Aspergillus infections occur at a time of leukopenia and profound immunosuppression. The time to develop leukopenia after TBI was very reproducible in the beagles. At day 10–14 days after XRT, when the animal's absolute white blood cell count falls below about 500 per $\mu$L (neutrophil count <400 per $\mu$L), the mold spore administration was performed. The WBC remain at about <500 per $\mu$L till day 25–30 after TBI, at which time the count recovered fairly rapidly in animal's that had not been inoculated with Aspergillus spores, or in beagles who had been inoculated with a dose that was too low to yield progressive infection.

7. Supportive Care: The first few animal's died from a superimposed secondary bacterial infection rather than from the mold infection itself In addition, there were bleeding complications when the dogs' platelet count fell below 10,000 per $\mu$L. The inventors therefore decided to utilize prophylactic oral (broad-spectrum) antibiotics and "prophylactic" platelet transfusions. If an animal became depressed and febrile when leukopenic and immunosuppressed, the antibiotic regimen was changed as deemed necessary to obtain better antibacterial coverage, while still allowing for the mold infection to progress.

After considering the above seven parameters, and examining each problem in detail, the inventors developed a non-trivial large animal model that is relevant for the human situation where an immunocompromised patient suffers an opportunistic mold infection. The inventors contemplate that the model will allow longitudinal and systematic studies of the pathophysiology of the infection allowing the development of new antifungal therapies, such as antifungal agents and/or combination drugs with a high propensity for clinical success. The inventors already have such antifungals in initial trials. The inventors further envision that the model will allow methods for the early detection of local mold infection which may then be treated before progression to invasive disease sets in. The inventors further envision the use of this model for the long-term follow-up of treatment results and prognosis.

TABLE 1

Induction of Mold Infection in the Beagle Model

| Dog's # & (Fungal Dose) | TBI Dose Gy | Steroid | Pneumonia | Platelet/ Antibiotic | Complications |
|---|---|---|---|---|---|
| 2856721 ($1 \times 10^6$) | 3.0 | 20 mg | Yes | No | depressed with serosanguinous fluid from nares and mouth, died pancytopenic and septic (*P. aeruginosa* and *E. coli*) |
| 2869349 ($1 \times 10^6$) | 3.0 | 20 mg | Yes | No | depressed, dyspneic, cyanotic, pale mucous membranes, died pancytopenic with pneumonia |
| 2705583 ($1 \times 10^6$) | 3.0 | 20 mg | Yes | No | depressed, persistent cough, poor appetite, febrile, slight head tremor, died pancytopenic and septic (*E. Coli*) |
| 2694603 ($1 \times 10^6$) | 3.0 | 20 mg | Yes | No | dyspnea/tachypnea. Right lung sounds muffled, pale mucous membranes died pancytopenic and septic (*E. Coli*) |
| 2805928 ($1 \times 10^6$) | 2.1 | 20 mg | No | No | recovered 30 days post XRT |
| 2729903 ($1 \times 10^6$) | 2.1 | 20 mg | No | No | recovered 30 days post XRT |
| 2870908 ($1 \times 10^6$) | 2.5 | 20 mg | No | No | Alive with no infection |
| 2872242 ($1 \times 10^6$) | 2.5 | 20 mg | Yes | No | Aspergillus induced fungal pneumonia |
| 2872439 ($1 \times 10^6$) | 2.5 | 30 mg | No | No | Alive with no infection |
| 2873672 ($1 \times 10^6$) | 2.5 | 30 mg | No | No | Alive with no infection |
| 2867192 ($1 \times 10^6$) | 2.75 | 30 mg | Yes | No | depressed, dyspneic, cyanotic, pale Mucous membranes, died pancytopeni with Pneumonia |
| 2808919 ($1 \times 10^6$) | 2.75 | 30 mg | Yes | No | Mycotic pneumonia lung, euthanized |
| 2909944 ($1 \times 10^6$) | 2.75 | 30 mg | Yes | No | Depressed, bloody stools, anorexia, widespread hemorragic diathesis |
| 2916258 ($1 \times 10^6$) | 2.75 | 30 mg | Yes | No | Alive with no infection |
| 2876213 ($1 \times 10^6$) | 3.0 | 30 mg | Yes | No | Possible Candida-like organism seen in blood smear. Dog died, Aspergillus pneumonia at necropsy. |
| 2882078 ($1 \times 10^6$) | 3.0 | 30 mg | Yes | No | Dog died |
| 2991152 ($1 \times 10^6$) | 3.0 | 30 mg | Yes | Yes | severe depression, dyspnea, cyanosis, pale mucous membranes |
| 2917289 ($1 \times 10^6$) | 3.0 | 30 mg | Yes | Yes | severe depression, diarrhea appears to contain fresh blood, dog euthanized |
| CKLAGU ($2 \times 10^5$) | 3.0 | 30 mg | Pneumonia which improved | Yes | no discharge or bleeding. |
| 2915499 ($4 \times 10^5$) | 3.0 | 30 mg × 5 day | No | Yes | slightly depressed (blood positive for beta hemolytic strep) |
| 2911892 ($1 \times 10^6$) | 3.0 | 30 mg | Yes | Yes | slight depression, vomiting, poor appetite, administered supportive fluids, anorexia, diarrhea, |
| CKLADZ ($7 \times 10^5$) | 3.0 | 30 mg × 5 day | No | Yes | lesion in pleura, parenchyma was normal |

TABLE 1-continued

Induction of Mold Infection in the Beagle Model

| Dog's # & (Fungal Dose) | TBI Dose Gy | Steroid | Pneumonia | Platelet/ Antibiotic | Complications |
|---|---|---|---|---|---|
| 3062481 ($1 \times 10^6$) | 3.0 | 30 mg × 5 day | No | Yes | slightly depressed |
| 2938197 ($1 \times 10^6$) | 3.0 | 30 mg × 5 day | No | Yes | gross lesions on right lung, caudal lung had areas of discoloration and firm texture |
| 2940141 ($1 \times 10^6$) | 3.0 | 30/10 mg Cont. | Yes | Yes | moderate depression, anorexia, several puddles of blood in cage |
| 2905183 ($1 \times 10^6$) | 3.0 | 30/10 mg cont. | Yes | Yes | depression, bloody stool, diarrhea |
| CKLASI ($1 \times 10^6$) | 3.0 | 30/10 mg | No | Yes | no gross lesion on lung |
| 3030334 ($1 \times 10^6$) | 3.0 | 30/10 mg | Yes | Yes | trachea and bronchi filled with frothy fluid |
| 3121216 ($1 \times 10^6$) | 3.0 | 30/10 mg | Yes | Yes | only lesions found in right lung, cranial right diaphragmatic lobe had a small region with 3 to 12 mm tan nodules Dog survived pneumonia 4 weeks post therapy |
| 3124347 ($1 \times 10^6$) | 3.0 | 30/10 mg | Yes | Yes | only lesions found in right lung, cranial right diaphragmatic lobe had a small region with 3 to 12 mm tan nodules Dog survived pneumonia 4 weeks post therapy |
| 3090850 ($1 \times 10^6$) | 3.0 | 30/10 mg | Yes | Yes | only lesions found in right lung, cranial right diaphragmatic lobe had a small Region with 3 to 12 mm tan nodules |

*Natamycin therapy was instituted in the last 3 beagles a day after Aspergillus inoculum.
Natamycin extended life by 80% as compared to untreated animals Example 2

Data Obtained Using the Model

The complexity of the new model illustrates clearly the difficulty the inventors experienced in making the mold (*Aspergillus fumigatus*) infect a large animal. Only when a profoundly immunosuppressed state was obtained, could the inventors successfully and reproducibly infect the dogs. To obtain this immunosuppressed state the inventors decided to use a combination of total body irradiation (TBI) and steroids. This was based on the following considerations:

1. TBI is used as the basis for the majority of the current clinical bone marrow pre-transplantation conditioning programs, and it is considered as the equivalent of a clinical "golden standard" for pre-transplant conditioning therapy. Its main advantage remains in its reproducibility, an XRT dose can be standardized to within less than 5% of calculated/desired dose, whereas actual delivered systemic doses of most cytotoxic medications vary from two- to more than five-fold.

2. Steroids, which are very immunosuppressive, are clinically used to treat graft vs. host disease, and also used for several other reasons in the treatment of leukemia and in conjunction with the supportive care in the post transplant phase, and they contribute in an important way to the human immunosuppressed state which is a prerequisite for an opportunistic mold infection. In clinical oncological practice steroids are commonly considered to promote the spread of systemic fungal infections in immunosuppressed patients.

The inventors have now treated 31 beagles that are evaluable for a complete cycle of induction/progression of infection, that sometimes causes pneumonia, after TBI and steroids (see Table 1). The last three dogs, in Table 1, were also treated with daily intravenous Natamycin, a new antifungal agent, for 16 days as a test of the model.

The use of a dose of less than 3.0 Gy in the presented setting showed less reproducibility in the attainment of a fungal infection, and early cessation of the prednisolone after mold inoculation also commonly led to rejection of the infection by the animal. After a TBI dose of 3.0 Gy, and daily oral steroids (30 mg daily lowered to 10 mg daily after the fungal inoculation), the animal's developed profound pancytopenia in about ten days, and subsequently received a fungal inoculum. All the first four dogs developed signs compatible with a clinical fungal/mold pneumonia, fever, depression, anorexia, blood-tinged cough and a chest radiograph with a localized infiltrate in the right lower lung (see FIG. 3 for an example of the typical chest radiograph). Unfortunately, these dogs died from a clinical picture of sepsis/bacterial infection and blood cultures were positive for bacteria in three of the four dogs. Based on this finding, the inventors therefore instituted prophylactic antibacterial and anti-yeast therapy, as well as every-other-day platelet transfusions as soon as the platelet count was found to fall below 10,000 per $\mu$L. Subsequent animal's survived the challenge from bacterial agents and progressed to die in a clinical picture of respiratory failure/overwhelming progressive mold pneumonia (for microscopic detail of a lung lesion sectioned at necropsy, please see FIGS. 4 A, B, C).

The establishment of this beagle model has been a major undertaking, and there was previously no good animal model, i.e. model that closely resembles the human clinical scenario of a systemic mold/Aspergillus infection in an immunocompromised host that has been described in the available literature. The inventors envision that this accomplishment will lead to further investigations that will lead to an understanding of the pathophysiology of mold infections and therefore serve as a tool for developing new antifungal agents. As an example, the inventors have applied the model in the in vivo evaluation of Natamycin in three dogs. One animal experienced an increase in expected life span from nine days to 17 days after fungal inoculation, and two animal's rejected the infection after a 16-day cycle of daily Natamycin treatments. The latter two dogs remained free from resurgence of the mold infection for one month post completion of drug treatment, and at necropsy there were only signs of healing. Based on these data, the inventors contemplate that the new animal model presented herein will allow a continued in vivo evaluation of the toxicity and antifungal properties of new antifungal agents and that it will also be a valuable tool for the development of technology for early detection of mold infection and for the longitudinal assessment of treatment result.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anaissie, "Opportunistic mycoses in the immunocompromised host: experience at a cancer center and review," Clin. Infect. Dis., 14:S43–53, 1992.

Anaissie, Bodey, Rinaldi, "Emerging fingal pathogens," Eur. J. Clin. Microbiol. Infect. Dis., 8:323–330,1989.

Blazar, Hurd, Snover, Alexander, McGlave, "Invasive Fusarium infections in bone marrow transplant recipients," Am. J. Med., 77:645–651, 1984.

Boogaerts, Verhoef, Zachee, Demuynck, Verbist, DeBeule, "Antifingal prophylaxis with itraconazole in prolonged neutropenia: Correlation with plasma levels," Mycoses, 32:103, 1989.

Dixon, Polak, Walsh, "Fungus dose-dependent primary pulmonary Aspergillosis in immunosuppressed mice," Infect. and Immun., 1452–56, 1989.

Eisenstein, Biddinger, Rhodes, "Experimental murine invasive Aspergillosis," Am. J Clin. Pathol., 93:510–15, 1990.

Epstein, Verney, Miale, Sidransky, "Studies on he pathogenesis of experimental pulmonary Aspergillosis," Amer. J. Pathology, 51:769–788, 1967.

Francis, Lee, Hoffmnan, Peter, Francesconi, Bacher, Shelhamer, Pizzo, Walsh, "Efficacy of unilamellar liposomal Amphotericin B in treatment of pulmonary Aspergillosis in persistently granulocytopenic rabbits: the potential role of bronchoalveolar D-mannitol and serum galactomannan as markers of infection," J. Inf. Dis., 169:356–68, 1994.

Hector, Yee, Collins, "Use of DBA/2N mice in models of systemic Candidiasis and pulmonary and systemic Aspergillosis," Infect. and Immun., 1476–78, 1990.

Kurup and Shfth, "Experimental Aspergillosis in rabbits," Comp. Immun. Microbiol Infect. Dis. 4:161–174, 1981.

Lopez-Berestein, Bodey, Fainstein, Keating, Frankel, Zeluff, Gentry, Metha, "Treatment of systemic fingal infections with liposomal amphotericin B," Arch. Int. Med., 149:2533–36, 1989.

Lopez-Berestein, Hopfer, Metha, Metha, Hersh, Juliano, "Liposome-encapsulated amphotericin B for treatment of disseminated candidiasis in neutropenic mice," J. Infect Dis., 150:278–83, 1984.

Lopez-Berestein, Metha, Hopfer, Mills, Kasi, Metha, Fainstein, Luna, Hersh, Juliano, "Treatment and prophylaxis of disseminated Candida albicans infections in mice with liposome-encapsulated amphotericin B," J. Infect Dis., 147:939–45, 1983.

Morrison, Haake, Weisdorf, "The spectrum of non-Candida fingal infections following bone marrow transplantation," Medicine, 72:78–89, 1993.

Morrison, Haake, Weisdorf, "Non-Candida fungal infections after bone marrow transplantation: risk factors and outcome," Am. J. Med., 96:497–503, 1994.

Nawada, Amitani, Tanaka, Niimi, Suzuki, Murayama, Kuze, "Murine model of invasive pulmonary Aspergillosis following an earlier stage, noninvasive Aspergillus infection," J. Clin. Microbiol, 1433–39, 1996.

Pfaller and Wenzel, "Impact of the changing epidemiology of fungal infections in the 1990s," Europ. J. Clin. Microbiol. Infect. Dis., 11:287–291, 1992.

Sande and Mandell, "Antimicrobial agents, antifungal and antiviral agents. I. Antifingal agents: Amphotericin B," In: The pharmacological basis of therapeutics, MacMillan Publishing Company Inc., New York N.Y., 7:1219–1223, 1985.

Spreadbury, Krausz, Pervez, Cohen, "Invasive Aspergillosis: Clinical and pathological features of a new animal model," J. Med. and Vet. Mycology, 27:5–15, 1989.

Tollemar, Ringden, Andersson, Sundberg, Ljungman, Sparrelid, Tydén, "Prophylactic use of liposomal amphotericin B (AmBisome) against fungal infections: A randomized trial in bone marrow transplant recipients," Transplant Proc., 25:1495–97, 1993.

Turner, Hackshaw, Papadimitriou, Perrott, "The pathogenesis of experimental pulmonary Aspergillosis in normal and cortisone-treated rats," J. Pathol., 118: 65–73, 1976.

Uzun and Anaissie, "Antifingal prophylaxis in patients with hematologic malignancies. A reappraisal," Blood, 86:2063–72, 1995.

What is claimed is:

1. A canine model for invasive pulmonary fungal infection in an immunocompromised host consisting essentially of a beagle dog being rendered profoundly immunocompromised comprising an invasive pulmonary fungal infection, wherein the fungus is a common species causing pulmonary fungal infection or an opportunistic pulmonary infectious fungus, wherein symptoms of pulmonary fungal infection are present.

2. The canine model according to claim 1, wherein said fungus belongs to the Aspergillus species.

3. The canine model according to claim 2, wherein said fungus is *Aspergillus fumigatus*.

4. The canine model according to claim 1, wherein the beagle develops an initial localized infective lesion which progresses to a diffuse infection and eventually leads to the animal's death if left untreated.

5. A method for obtaining a canine model for invasive pulmonary fungal infection in an immunocompromised host comprising:

a) obtaining a beagle dog;

b) immunocompromising said beagle; and c) infecting said beagle with a fungus.

6. The method of claim 5, wherein the immunocompromization of the beagle is achieved by total body irradiation.

7. The method of claim 6, wherein the total body irradiation further comprises X-ray-cobalt irradiation.

8. The method of claim 6, wherein the immunocompromization further comprises the administration of steroids.

9. The method of claim 5, wherein said infecting is by a localized infecting of pulmonary tissue with said fungus.

10. The method of claim 5, wherein said infecting is achieved by repeated infection with the fungus.

11. The method of claim 5, wherein said infecting is performed using a bronchoscope.

12. The method of claim 11, wherein said bronchoscope is a pediatric bronchoscope.

13. The method of claim 5, wherein said infecting is performed when the beagle has leukopenia.

14. The method of claim 5, wherein said infecting is performed when the beagle has immunosuppression.

15. The method of claim 5, wherein said infecting is performed when the beagle has a neutrophil count of <about 400 per µL.

16. The method of claim 5, wherein said fungus belongs to the Aspergillus species.

17. The method of claim 5, wherein said fungus is *Aspergillus fumigatus.*

18. The method of claim 5, further comprising administering to the beagle a standard cancer therapy.

19. A method for evaluating an antifungal agent for treating a pulmonary fungal infection in an immunocompromised host, comprising:
   a) providing an immunocompromised beagle which has been infected with a fungus;
   b) administering the agent to said beagle;
   c) measuring one or more symptoms of fingal infection; and
   d) comparing said symptoms to the symptoms of an immunocompromised infected beagle not treated with the agent,
      wherein an improvement in the symptoms of the beagle treated with the agent, as compared to the symptoms of the beagle not treated with the agent, indicates that the agent is an antifungal agent.

20. The method of claim 19, wherein said antifingal agent further comprises a combination of pharmaceutical agents.

21. The method of claim 19, wherein the immunocompromised beagle is further administered standard cancer therapies.

22. The method of claim 19, wherein the symptoms comprise fever, loss of appetite, depression, and changes in chest-X-rays in the beagle.

23. The method of claim 19, further comprising comparing said symptoms to the symptoms of an uninfected immunocompromised beagle treated with the agent.

* * * * *

Disclaimer 6,444,872—Borje S. Andersson, Houston, TX. LARGE ANIMAL MODEL OF INVASIVE PULMONARY ASPERGILLOSIS IN AN IMMUNOCOMPROMISED HOST. Patent dated Sep. 03, 2002. Disclaimer filed May 26, 2004, by the assignee, Board of Regents, The University of Texas System.

Hereby enters this disclaimer to the remaining term of said patent.

*(Official Gazette March 22, 2005)*

US006444872C1

(12) INTER PARTES REEXAMINATION CERTIFICATE (0005th)
United States Patent
Andersson et al.

(10) Number: US 6,444,872 C1
(45) Certificate Issued: Aug. 15, 2006

(54) LARGE ANIMAL MODEL OF INVASIVE PULMONARY ASPERGILLOSIS IN AN IMMUNOCOMPROMISED HOST

(75) Inventors: Borje S. Andersson, Houston, TX (US); Taraneh K. Sadeghi, Houston, TX (US); Douglas M. Cromeens, Spring, TX (US); Jeffrey J. Tarrand, Houston, TX (US)

(73) Assignee: The University of Texas System Board of Regents, Austin, TX (US)

Reexamination Request:
No. 95/000,037, Feb. 25, 2004

Reexamination Certificate for:
Patent No.: 6,444,872
Issued: Sep. 3, 2002
Appl. No.: 09/642,397
Filed: Aug. 18, 2000

Disclaimer of Claims 1 to 23 Filed May 26, 2004 (O.G. citation Mar. 22, 2005)

Related U.S. Application Data
(60) Provisional application No. 60/149,948, filed on Aug. 19, 1999.

(51) Int. Cl.
A01K 67/00 (2006.01)
A01K 67/27 (2006.01)
G01N 33/00 (2006.01)
G01N 33/53 (2006.01)
A61F 2/00 (2006.01)
C12Q 1/00 (2006.01)

(52) U.S. Cl. .................... 800/11; 800/14; 424/423; 435/4; 435/7.2; 435/7.31

(58) Field of Classification Search .............. 800/11, 800/14, 8, 9; 424/423; 435/4, 7.31, 7.2
See application file for complete search history.

(56) References Cited

U.S. PATENT DOCUMENTS 5,833,946 A  11/1998  Tamburini et al. ........... 424/9.2

OTHER PUBLICATIONS

Ruthe, "Experimental Granulocyte Transfusions in the Control of Systematic Candidiasis in the Leukopenic Host", Blood, vol. 52, #3, (Sep. 1978), pp. 493–498.

Dagle, et al. "Atlas of Experimentally–Induced Neoplasia in Beagle Dogs", Dep't of Energy Doc. #PNNL–11358, (G.E. Dagle, et al., eds.) Oct. 1996, pp. I–viii.

Thomas Lathrop Stedman, "Stedman's Medical Dictionary", 25th Edition, 1990, Baltimore: Williams & Wilkins. pp. 86, 142, 668,766,768,798,862,909, 1051, and 1265.

Schick, et al. "Experimental Lobar Pneumonia in Canine Lung Grafts", Surgery, vol. 75, #3, pp. 348–356, Mar. 1974.

Reynolds, et al. "Changes in the Composition of Canine Respiratory Cells Obtained by Bronchial Lavage following Irradiation or Drug Immunosuppression", Proc. Soc. Exp. Biol. and Med., 151, pp. 756–761 (1976).

(Continued)

*Primary Examiner*—Ram R. Shukla

(57) ABSTRACT

A model of systemic mold/Aspergillus infection in a profoundly immunocompromised host has been established in the beagle dog. The beagle was rendered immunosuppressed using a combination of total body irradiation and daily steroids, which provided a window of time where the mold could be successfully inoculated through a bronchoscope. This created a localized infection in one lung lobe, which subsequently spread diffusely throughout the lung parenchyma, and uniformly resulted in the animal's death. The invention contemplates the further study of the pathophysiology of opportunistic mold infections in vivo and also provides examples for the development of new antifungal agents and more effective combinations of agents. Finally, the invention contemplates the development of technology for the early detection of systemic mold infections. The inventors envision, that the use of the model should help save patients from clinical trials of antifungal drugs that may be effective in vitro without living up to the expectations in a clinical setting.

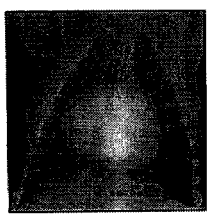

OTHER PUBLICATIONS

Venker–van–Haagen, A.J. "Aspergillosis in the Dog: Introduction and Short Review of the Literature". Tijdschrift voor Diergeneeskunde, vol. 116, Suppl. 1 (Apr. 1991), p. 34S.

Weber, et al. "Treatment of Systemic Candidiasis in Neutropenic Dogs with Ketoconazole", Exp. Hematol., vol. 13, 1985, pp. 791–795.

Michaelson et al. "Radiation Time–Intensity and Pathophysiologic Correlations in Whole and Partial–Body–X–r-radiated Beagles irradiated Beagles",Proceedings of a Symposium on Dose Rate in Mammalian Radiation Biology, (1968), USAEC–CONF–681410.

Springmeyer, et al. "Alveolar Macrophage Kinetics and Function after Interruption of Canine Marrow Function", Am. Rev. Respir. Dis., (1982), vol. 125, pp. 347–351.

Morrison et al. "Non–Candida Fungal Infections After Bone Marrow Transplantation: Risk Factors and Outcome", American Journal of Medicine, vol. 96, pp. 497–503 (Jun. 1994).

Farrell et al. "Experimental Canine Histoplasmosis with Acute Fatal and Chronic Recovered Courses", Am. J. Pathology, col. 53, #3, pp. 425–446 (Sep. 1968).

Southard. "Bronchopulmonary Aspergillosis in a Dog", J. Am. Veterinary Med. Assoc., vol. 190, #7, pp. 875–877 (Apr. 1987).

Spreadbury et al. "Invasive Aspergillosis: Clinical and Pathological Features of a New Animal Model", J. Med. and Vet. Mycology, vol. 27, pp. 5–15 (1989).

Leesti, M., Decision of the Commissioner of Patents of Canada published Aug. 4, 1995, Decision No. 1203, Application No. 484723, available at http://tinyurl.com/2fuch, last accessed Feb. 18, 2004.

Nadon J., Decision of the Fed. Court of Can. Trial Div., *Harv. Coll.* v. *Canada (Comm'r of Patents)*, [1998]. 3 F.C. 510. (Can.). Date published: Apr. 21, 1998.

International Preliminary Examination Report for PCT Publication PCT/US00/22895, issued Nov. 5, 2001, by G. Hillenbrand, European Patent Office, Munich DE, pp. 1–5.

Smith, D.A., et al. "Disseminated Mycosis: A Danger with Systemic Corticosteroid Therapy", Can. Vet. J., vol. 22, p. 276 (Sep. 1981).

Chow, H.S., et al. "Experimental Candidiasis in Neutropenic Dogs: Tissue Burden of Infection and Granulocyte Transfusion Effects", Blood, vol. 59, #2, (Feb. 1982), pp. 328–333.

Vriesendorp, H.M., "Bone–Marrow Transplantation in the Canine", in Shifrine, M., ed. "The Canine as a Biomedical Research Model", US DOE/TIC–10191 (1980)., pp. 153–155, 181–182, 194–195.

Ohshima, K–I. Et al. "Mycotic Bronchitis in a Dog Affected with Distemper", Jap. J. Vet Sci., vol. 41, pp. 83–87 (1979).

Sukura, A. "Occurrence of Pneumocystis Carinii in Canine Distemper", Acta. Vet. Scand., vol. 38, pp. 201–205 (1997).

Kappe, R. et al. "Mechanism of Host Defence Against Fungal Infection", J. Med. Vet. Mycology (1992), vol. 30, Supplement 1, apges 167–177.

Ebert, J.W., et al. "Experimental Canine Histoplasmosis and Blastomycosis", Mycopathologia et Mycologia Applicata, vol. 45, #3–4, apges 285–300 (1971).

Walsh, T.J. et al. "Immunomodulation and Antifungal Therapy of Experimental Invasive Candidosis, Histoplasmosis, and Aspergillosis . . . ", J. Med. Vet. Mycology, (1992), vol. 30, Supplement 1, pp. 225–240.

Roilides, E. et al. "Prevention of Corticosteroid–Induced Suppression of Human Polymorphonuclear Leukocyte–Induced Damage of Aspergillus Fumigatus Hyphae . . . ", Infection and Immunity, 61, #11 (1993), pp. 4870–4877.

Silva–Ribeiro, V.L., et al. "Canine Histoplasmosis in Rio de Janeiro: Natural and Experimental Infections", J. Med. Vet. Mycology (1987), vol. 25, pp. 319–322.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–23 are now disclaimed.

\* \* \* \* \*